(12) United States Patent
Lin

(10) Patent No.: US 6,248,071 B1
(45) Date of Patent: Jun. 19, 2001

(54) DEMODULATING WIDE-BAND ULTRASOUND SIGNALS

(75) Inventor: Shengtz Lin, Cupertino, CA (US)

(73) Assignee: U-Systems, Inc., Los Altos, CA (US)

( * ) Notice: Subject to any disclaimer, the term of this patent is extended or adjusted under 35 U.S.C. 154(b) by 0 days.

(21) Appl. No.: 09/493,969

(22) Filed: Jan. 28, 2000

(51) Int. Cl.$^7$ ..................................................... A61B 8/00
(52) U.S. Cl. ........................................... 600/443; 600/455
(58) Field of Search ................................... 600/455, 456, 600/457, 443, 447, 448, 449, 444

(56) References Cited

U.S. PATENT DOCUMENTS

| | | |
|---|---|---|
| 5,482,044 | 1/1996 | Lin et al. . |
| 5,544,659 * | 8/1996 | Banjanin ............................ 600/455 |
| 5,664,575 * | 9/1997 | Banjanin et al. ..................... 600/455 |
| 6,123,672 * | 9/2000 | Miller et al. ........................ 600/455 |

OTHER PUBLICATIONS

James A. Zagzebski, *Essentials of Ultrasound Physics* (1996) (title page and table of contents).
www.intersil.com/data/fn/fn3/fn3365/fn3365.pdf.
www.intersil.com/data/an/an9/an9063/an9603.pdf.
Carlson, *Communication Systems: An introduction to Signals and Noise in Electrical communication*, (McGraw–Hill, 3rd ed. 1986).
Couch, *Digital And Analog Communications System*, (MacMillan, 3rd ed. 1990) at pp. 497–503.

* cited by examiner

*Primary Examiner*—Marvin M. Lateef
*Assistant Examiner*—Maulin Patel
(74) *Attorney, Agent, or Firm*—Cooper & Dunham LLP

(57) ABSTRACT

A demodulator for use in an ultrasound information processing system is described, where in a preferred embodiment the demodulator uses a half-band filter to perform mirror-cancellation during the demodulation process. The demodulator comprises a mirror canceling quadrature mixer that mixes the input signal with quarter-sampling-frequency sinusoids and then low-pass-filters the mixed signals with half-band filters having a cutoff frequency of one-fourth the sampling frequency. In an ultrasound demodulator in accordance with a preferred embodiment, a significantly sharper mirror cancellation on the wideband input signal is achieved. Additionally, the number and complexity of mirror canceling filter operations significantly reduced, allowing for easier hardware implementation using less expensive, off-the-shelf components. Furthermore, simplified hardware for digitally providing harmonic imaging applications is achieved.

33 Claims, 13 Drawing Sheets

DEMODULATING WIDE-BAND ULTRASOUND SIGNALS

FIELD

This patent specification relates to the field of ultrasound information processing systems. In particular, it relates to a method and system for the demodulation of ultrasound signals for use in ultrasound systems.

BACKGROUND

In recent decades ultrasonic imaging technology has played an increasing role in examining the internal structure of living organisms. The technology has applications in diagnosis of various medical ailments where it is useful to examine structural details in soft tissues within the body. Ultrasound imaging systems are advantageous for use in medical diagnosis as they are non-invasive, easy to use, and do not subject patients to the dangers of electromagnetic radiation. Instead of electromagnetic radiation, an ultrasound imaging system transmits sound waves of very high frequency (e.g., 2 MHz to 10 MHz) into the patient and processes echoes reflected from structures in the patient's body to form two dimensional or three dimensional images.

More recently, ultrasonic imaging systems have been able to detect blood flow as well as tissue amplitude along the axis of the interrogating ultrasonic wave. These blood velocities are related by the Doppler effect movement within the body and blood flow is information of high diagnostic significance for certain diseases. This and other ultrasound background information is disclosed in Zagzebski, *Essentials of Ultrasound Physics* (Mosby 1996), the contents of which are hereby incorporated by reference into the present disclosure.

Signal demodulation represents a key preliminary step in converting reflected ultrasound signals into a usable representation on an output display. FIGS. 1A and 1B show exemplary plots of ultrasonic waves as transmitted into the body and received from the body, respectively, by an ultrasound transducer (not shown). In a typical ultrasound system operating in pulse-echo mode, the transducer transmits a signal 100 comprising a series of time-limited modulated bursts as shown in FIG. 1A, and then receives a reflected signal 102 as shown in FIG. 1B. The plot 100 of FIG. 1A is of a generic voltage signal which, as known in the art, is converted into sound waves by piezoelectric devices in the transducer for transmission into the body. The plot 102 of FIG. 1B is likewise a generic voltage signal resulting from the conversion of reflected sound waves into voltages by the piezoelectric devices in the probe.

It is to be appreciated for purposes of the present disclosure that system specifics such as frequency ranges, pulse durations, and the like are given by way of example only and are not intended to limit the scope of the preferred embodiments. By way of example and not by way of limitation, typical parameters for real-time ultrasound imaging applications would include: a carrier frequency $F_c$ of 8 MHz (depending on the application, ultrasound implementations may use $F_c$ selected from the range 2 MHz–15 MHz); a burst repetition frequency BRF of 2000 Hz, i.e., 1 burst is sent every 500 μs (real-time imaging systems may use a BRF selected from the range 2000 Hz–4000 Hz); and a burst duration BD of 1 μs. As shown in FIG. 1B, the reflected signal x(t) in plot 102 can be expressed as a sinusoid at the carrier frequency $F_c$ modulated by an envelope signal A(t) and a time-varying phase term φ(t), as can be expressed by Equations (1)–(3):

$$x(t)=A(t)\cos\{\omega_c t+\phi(t)\} \quad \{1\}$$

$$\omega_c=2\pi F_c \quad \{2\}$$

$$x(t)=Re\{A(t)e^{j\phi(t)}e^{j\omega_c t}\} \quad \{3\}$$

Depending on the ultrasound implementation, it is the content of the envelope signal A(t) and/or the content of the phase signal φ(t) that is of interest in generating the ultrasound system display output. For example, in B-mode imaging it is the envelope signal A(t) that is of interest because A(t) is proportional to the reflective index of the target tissue. As another example, in Doppler mode imaging it is the phase signal φ(t) that is of interest because as the velocity of fluid flow in the target area is proportional to its first derivative dφ/dt. Because the basic analytic signal $A(t)e^{j\phi(t)}$ modulated by the carrier frequency $F_c$ in Equations (1)–(3) is usually found to contain frequency content in the several-megahertz range, which is not significantly less than the carrier frequency $F_c$, the resultant signal x(t) is generally classified as a wideband signal.

FIG. 1C shows frequency spectra 104, 106, and 108 of the wideband signal x(t) corresponding to differing exemplary target depths of 1 cm, 10 cm, and 20 cm, respectively. The spectra 104, 106, and 108 correspond to the amplitude of the Fourier transform X(f) of the signal x(t) taken over small intervals of time around points corresponding to the expected arrival time of burst reflections from depths of 1 cm, 10 cm, and 20 cm, respectively. As illustrated by FIG. 1C, the frequency spectrum X(f) is time varying in its characteristics. As known in the art, this is due to a frequency and depth attenuation factor of about 0.6 dB/MHz-cm for a typical ultrasound system on a typical human target, which causes the spectrum to be increasingly skewed toward lower frequencies in the far field (i.e., at greater depths) than in the near field (i.e., at lesser depths). Accordingly, there are different half-power bandwidths W of the analytic signal $A(t)e^{j\phi(t)}$ as a function of depth, and in general $W_{depth=d1}>W_{depth=d2}$ for d2>d1. For purposes of clarity of disclosure, and not for purposes of limiting the scope of the preferred embodiments, the analytic signal $A(t)e^{j\phi(t)}$ is characterized herein as having a generic upper frequency limit W/2, where W is a half-power bandwidth for a depth in the near field. It is to be understood, however, that in practical systems a modified value for the upper frequency limit may be used without departing from the scope of the preferred embodiments.

FIG. 2 shows a block diagram of a conventional ultrasound system 200 in accordance with prior art. Ultrasound system 200 comprises a transducer 202, a front end processor 204, a demodulator 206, and an amplitude detector and display apparatus 208. As described supra, transducer 202 transmits focused acoustic signals into the body and sends an analog response signal to front end processor 204. Front end processor 204 performs preliminary operations such as depth gain compensation and then transmits the result, commonly called the RF signal, to demodulator 206. For purposes of clarity and simplicity, the analog signal x(t), shown as plot 102 of FIG. 1B, is referred to herein as the RF signal, with depth gain compensation and/or other preliminary processing having already been performed by front end processor 204.

In the system of FIG. 2, the demodulator 206 performs processing steps directed to extracting the envelope signal A(t) and the phase signal φ(t) from the RF signal x(t), and then transmits the result to amplitude detector and display apparatus 208 for downstream processing and eventual image display. In a simplest form, for B-mode processing such a demodulator could simply comprise an analog envelope detector having a full-wave rectifier and a low-pass filter, as described in Carlson, *Communication Systems: An Introduction to Signals and Noise in Electrical Communication* (McGraw-Hill, 3$^{rd}$ ed. 1986), the contents of which are hereby incorporated by reference into the present disclosure. However, in most practical ultrasound systems in which both the amplitude signal A(t) will be desired for a B-mode processing mode, and where phase signal φ(t) will be desired for Doppler processing mode, a coherent detection scheme is used wherein demodulator 206 comprises a quadrature mixer. While older prior art implementations were analog in nature, most newer implementations are digital. For purposes of the present disclosure, and without loss of generality, it may be presumed that front end processor 204 incorporates an anti-aliasing filter followed by an analog to digital converter operating at a sampling frequency of $F_s$.

FIG. 3 shows a block diagram of demodulator 206 in accordance with prior art. Demodulator 206 comprises a local oscillator 302, mixers 304 and 306, and low pass filters 308 and 310. In accordance with conventional digital signal processing principles, the sampling frequency $F_s$ is at least satisfying the Nyquist rate, which for the system of FIG. 3, $2(F_c+W/2)$ is selected where, as described supra, $F_c$ is the ultrasound carrier frequency and W/2 is the upper frequency limit W/2 of the analytic signal $A(t)e^{j\Phi(t)}$. Upon sampling, the digitized RF signal x(kT) results, with the sampling period being $T=1/F_s$, the signal x(kT) simply being cast herein as x(k). Local oscillator 302 is designed to generate sinusoids at a mixing frequency $F_x$ that are in quadrature phase with each other, e.g., $\cos(2\pi F_x k)$ and $\sin(2\pi F_x k)$. Mixers 304 and 306 multiply the digitized RF signal x(k) with the respective quadrature-phase signals from the local oscillator 302, and the products are sent to low-pass filters 308 and 310, respectively. Low-pass filters 308 and 310 are designed to have sharp rolloffs at the upper frequency limit W/2 of the analytic signal $A(t)e^{j\Phi(t)}$.

As known in the art, for Doppler processing the mixing frequency $F_x$ is fixed at a frequency identical to the carrier frequency $F_c$. Using relationships known in the art and as described generally in Carlson, supra, in such case the demodulator 206 generates the signals I(k) and Q(k), where I(k) and Q(k) are related to the amplitude signal A(t) (expressed herein as A(k) in the digital domain) and phase signal φ(t) (expressed herein as φ(k) in the digital domain) as shown in Equations (4)–(8) below:

$$A(k)e^{j\phi(k)}=I(k)+jQ(k) \quad \{4\}$$

$$I(k)=A(k)\cos\phi(k) \quad \{5\}$$

$$Q(k)=A(k)\sin\phi(k) \quad \{6\}$$

$$A(k)=\sqrt{\{I^2(k)+Q^2(k)\}} \quad \{7\}$$

$$\phi(k)=\tan^{-1}\{Q(k)/I(k)\} \quad \{8\}$$

For B-mode processing, where it is desirable to obtain amplitude A(k) and where detection of phase φ(k) is not important, the mixing frequency $F_x$ is selected to be time-varying for increasing the signal-to-noise ratio. In particular, the mixing frequency $F_x$ is selected to correspond to an instantaneous center frequency of the signal x(t) which, as shown in FIG. 1C, becomes increasingly lower than the carrier frequency $F_c$ as the field depth increases. In such case, the oscillator 302 is a swept frequency oscillator, with the mixer frequency $F_x$ varying from a maximum value to a minimum value over each burst period BP. As known in the art, using a swept oscillator for the mixing frequency $F_x$ provides better signal-to-noise performance and therefore better detection of A(k) as compared to using a mixing frequency $F_x$ fixed at the carrier frequency $F_c$. However, it can also become impractical to recover the phase signal φ(k) using this method.

By way of nonlimiting example, and further to the example of FIG. 1C, for B-mode processing the mixing frequency $F_x$ may sweep from a maximum of 7.5 MHz in the near field to 5.0 MHz in the far field. It can be shown for such B-mode processing that the amplitude signal A(k) can still be computed from the demodulator 206 outputs I(k) and Q(k) from Equation (7) above while, as discussed supra, the phase signal φ(k) is generally not computed.

FIG. 4, comprising parts 4-1 and 4-2 shows Fourier spectrum plots corresponding to the operation of prior art demodulator 206 of FIG. 3. FIG. 4 shows a first plot 402 of the Fourier transform X(f) of the RF signal x(k), a second plot 404 of the Fourier transform of the local oscillator output $\cos(\omega_x kT)$, a third plot 406 of the Fourier transform of the mixer 304 output, a fourth plot 410 of the Fourier transform of the local oscillator output $\sin(\omega_x kT)$ as multiplied by j, and a fifth plot 412 of the Fourier transform of the mixer 306 output as multiplied by j. Note that Fourier transform plots 402, 406, and 412 repeat at intervals of $F_s$ as they represent digital signals at a sampling frequency of $F_s$, and only the frequency range of $-F_s$ to $F_s$ is shown.

Several problems, however, arise in ultrasound systems using the prior art wideband demodulator scheme of FIGS. 2 and 3. As shown on spectrum plots 406 and 412, the low-pass filters 308 and 310 must each have a frequency characteristic similar to the filter characteristic 408 for appropriate mirror rejection, i.e. cancellation of the undesired mirror portion of the mixed signals that occur at the output of mixers 304 and 306, respectively. As shown in FIG. 4, filter characteristic 408 of low-pass filters 308 and 310 is required to have a very sharp roll-off for proper construction of the signals I(k) and Q(k), respectively. In FIG. 4, for example, it is shown that the distance between the desired signal and its undesired mirror signal is approximately $(F_s-2F_c-W)$ if $F_s<2(F_c+F_x)$, and approximately $2(F_x-W)$ if $F_s>=2(F_c+F_x)$. Using the exemplary parameters of FIG. 4, this distance is only 32-2(8)-6.4=9.6 Mhz. Implementing this sharp roll-off, however, can create large group delay distortion at the filter band edge that degrade images produced from these signals and cause ringing. Additionally, using prior art ultrasound sampling and filter frequencies, the computations for implementing the low pass filters 308 and 310 are complex and time consuming, requiring general purpose digital signal processors of a very high order and very high power. Disadvantageously, the hardware needed to implement the prior art demodulator suffers from increased size, heat dissipation requirements, cost, and complexity due to the need for the sharp roll-off characteristic of low pass filters 308 and 310.

An additional problem with prior art demodulators as in FIG. 3 arises in the context of B-mode processing, which usually incorporates a swept mixing frequency $F_x$ at local oscillator 304 as described supra. Because the cutoff frequency of each of the low pass filters 308 and 310 is fixed at a single value, the mirror cancellation performed by low pass filters 308 and 310 is inherently better for certain values of mixing frequency $F_x$ than others. A undesirable design choice is forced upon the ultrasound hardware designer.

Given this dilemma, the design choice is usually made to select the cutoff frequency of the filters 308 and 310 such that near field reflections receive better mirror-canceling performance than far-field reflections. As a result of this design choice, there is inferior demodulation of far-field reflections as compared to near-field reflections.

One attempted prior solution to the above problems is described in U.S. Pat. No. 5,482,044, the contents of which are hereby incorporated by reference into the present application. The method described therein, however, which includes the use of a Hilbert transform, suffers from practical implementation difficulties and complexities, including problems related to the fact that the Hilbert transform is a noncausal signal which is not realizable in a physical system and can only be approximated.

A further problem with the prior art ultrasound information processing system of FIGS. 2 and 3, as well as U.S. Pat. No. 5,482,044, supra, is found in the context of harmonic imaging. As known in the art, in harmonic imaging mode an ultrasound information processing system attempts to recover second harmonic information near $2F_c$. The above cited prior art systems, however, provide no easy digital solution to the recovery of the second harmonic information, and in field implementations there is usually an analog high pass filter incorporated into the front end processor 204 that removes, in the analog domain, the information near $F_c$. The requirement to include an adjustable analog filter in the front end processor 204 with sufficient high pass characteristics presents problems of cost and complexity that it would be to desirable to avoid.

Accordingly, it would be desirable to provide an ultrasound demodulator having an improved output with better mirror canceling, less group delay distortion, and less ringing.

It would be further desirable to provide an ultrasound demodulator having an improved output while also being easier to implement in hardware, using lower cost, off-the-shelf components with lesser footprint and heat dissipation requirements.

It would be still further desirable to provide an ultrasound demodulator that, in amplitude-only implementations having swept-frequency mixing at a local oscillator, produces improved output in the far field as well as the near field.

It would be still further desirable to provide an ultrasound information processing system having the capability of performing harmonic imaging using low-cost, off-the-shelf components that implement a digital technique incorporated into the ultrasound demodulator hardware, and not requiring an analog high pass filter at a front end processor of the ultrasound information processing system.

SUMMARY

A demodulator for use in an ultrasound information processing system is provided, where in a preferred embodiment the demodulator uses a half-band filter to perform mirror-cancellation during the demodulation process. The demodulator can comprise a mirror canceling quadrature mixer that mixes the input signal with quadrature phase sinusoids oscillating at one-fourth of the sampling frequency, and then low-pass-filters the results with half-band filters having a cutoff frequency equal to one-fourth the sampling frequency. It has been found that in an ultrasound demodulator in accordance with a preferred embodiment, a significantly sharper mirror cancellation on the wideband input signal is achieved. Additionally, the number and complexity of mirror canceling filter operations is significantly reduced, allowing for easier hardware implementation using less expensive, off-the-shelf components. Furthermore, simplified hardware for digitally providing harmonic imaging applications is achieved.

An ultrasound information processing system for which the demodulator is suitable can comprise an ultrasound transducer generating acoustic bursts at a carrier frequency, the ultrasound transducer receiving acoustic echo signals and generating an input signal therefrom. The ultrasound information processing system filters the input signal with an anti-aliasing filter and digitizes the input signal at a sampling frequency to generate digital samples. A demodulator in accordance with the preferred embodiments comprises a quadrature mixer adapted to multiply the digital samples with quadrature-phase sinusoids at one quarter of said sampling frequency and to filter the results with half-band filters, each having a cutoff frequency of one-quarter of the sampling frequency, to produce mirror-cancelled signals. The demodulator further includes a complex mixer for rotating the mirror-canceled signals to baseband, whereby amplitude and phase information of the desired demodulated signal can be derived from said complex mixer output signals. The complex mixer is provided with mixing signals from a secondary local oscillator, the mixing signals being sinusoids at a frequency equal to the carrier frequency minus a first frequency function. For Doppler mode imaging, the first frequency function is fixed at the carrier frequency. For B-mode-imaging, the first frequency function may be a swept frequency function.

In accordance with a preferred embodiment, a programmable low-pass filter is provided at each output of the complex mixer, and an integrate-and-dump matched filter is provided at the output of each programmable low-pass filter. Advantageously, a harmonic imaging mode may be achieved by setting the first frequency function of the secondary local oscillator substantially near a frequency equal to twice the carrier frequency, and by adjusting the programmable low-pass filter to have a notch at the carrier frequency. Using these settings, the output of each programmable low-pass filter comprises a signal containing second harmonic information and suppressing first harmonic information.

DETAILED DESCRIPTION

Figure 5:
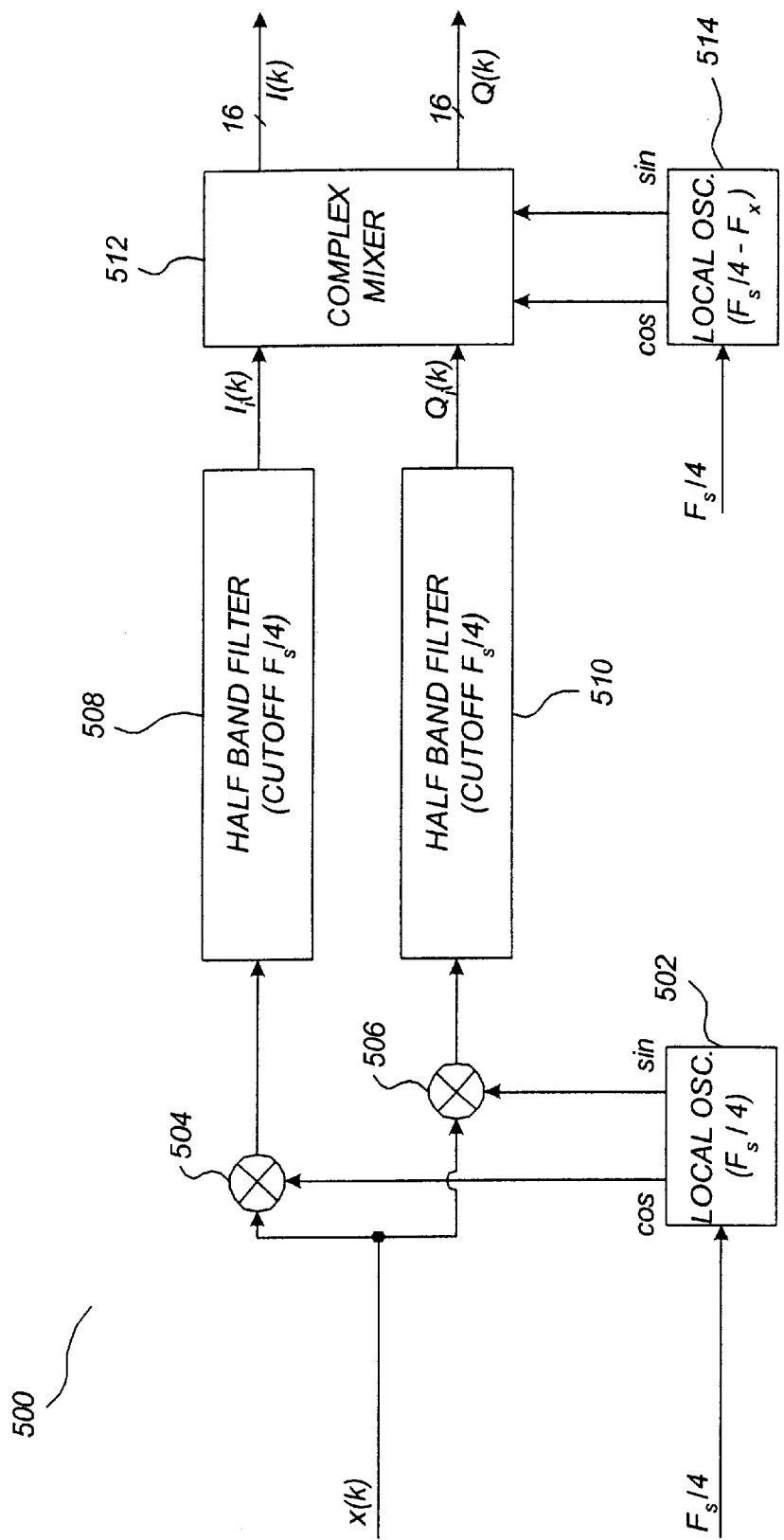
FIG. 5 is a block diagram of a demodulator for use in an ultrasound information processing system in accordance with a preferred embodiment.

FIG. 5 shows a block diagram of a demodulator 500 for use in an ultrasound information processing system in accordance with a preferred embodiment. It is to be appreciated that in the following description, specific parameters that are presented are done so by way of example so as to help illustrate and describe preferred embodiments, and are not presented by way of limitation. Demodulator 500 optionally comprises in an anti-aliasing filter (not shown) and an analog-to-digital converter (not shown) operating at a sampling frequency $F_s$. The anti-aliasing filter and the analog-to-digital converter may alternatively be considered as part of a front end processor located in front of the demodulator 500. Demodulator 500 comprises a first stage local oscillator 502, mixers 504 and 506, half-band filters 508 and 510, a complex mixer 512, and a secondary local oscillator 514. Inputs to demodulator 500 include the wideband signal x(k) that has been sampled at a sampling frequency of $F_s$, and outputs include an in-phase component signal I(k) and a quadrature-phase component signal Q(k). The desired envelope signal A(k) is related to I(k) and Q(k) by equation (7) supra and, for Doppler mode processing, the phase signal φ(k) is related to I(k) and Q(k) by equation (8) supra. The sampling frequency $F_s$ is selected such that it is at least twice as great as the highest frequency in the wideband signal x(t). In a preferred embodiment, the sampling frequency $F_s$ is 48 MHz.

An anti-aliasing filter (not shown) is used to filter out unwanted noise or unnecessary signals from the input signal x(t) above the Nyquist frequency of analog-to-digital converter (not shown) in order to prevent aliasing in the analog-to-digital converter. The Nyquist frequency is one half the sampling frequency, i.e., $F_s/2$. The cutoff frequency of the anti-aliasing filter is preferably below 15 MHz but must be large enough to accommodate the information in the signal x(t). Using the exemplary parameters of $F_s$= 48 MHz, $F_c$=8 MHz, and W=0.8 Fc as described in this patent specification, a cutoff frequency of 15 MHz is allowable as the upper frequency limit of the signal x(t) is not above 11.2 MHz. The output of the anti-aliasing filter is supplied to the analog to digital converter where it is sampled at the sampling frequency $F_s$, and the sampled signals are digitized. The digitized samples are denoted herein as x(k).

As shown in FIG. 5, demodulator 500 comprises a first stage local oscillator 502 for producing quadrature sinusoids at one-fourth the sampling frequency, i.e. at $F_s/4$. According to a preferred embodiment, the frequency $F_s/4$ of the first stage local oscillator 502 is advantageously selected such that mirror canceling operations may be subsequently performed by half band filters. The quadrature sinusoids at the output of the first stage local oscillator 502 are then multiplied by the signal x(k) at mixers 304 and 306, respectively. The formulae for the sinusoids generated by first stage local oscillator 502 are given below in Equations. (9)–(10):

$$\cos\{2\pi(F_s/4)(kT)\}=\cos(k\pi/2)=\{1, 0, -1, 0, 1, 0, -1, 0, \ldots\} \quad \{9\}$$

$$\sin\{2\pi(F_s/4)(kT)\}=\sin(k\pi/2)=\{0, 1, 0, -1, 0, 1, 0, -1, \ldots\} \quad \{10\}$$

As reflected in equations (9)–(10), the use of $F_s/4$ as the oscillation frequency for the first stage local oscillator 502 results in an especially simple operation for the digital mixers 504 and 506 that avoids the need for any actual multiplications. Since the oscillator signal is zero for every other term of the cosine and sine components as shown in Equations (9)–(10), the output of each mixer 504 and 506 can automatically be decimated to one-half the sampling frequency, $F_s/2$, with a simple alignment in time delay. Further, since the non-zero values of the oscillator signal alternate between 1 and −1, the mixing of these values with the sampled signals can be accomplished simply by inverting every other sample.

The signals from mixers 504 and 506 are fed to first stage half-band filters (HBF) 508 and 510. Advantageously, in accordance with a preferred embodiment, the use of a half-band filter having a passband between $-F_s/4$ and $F_s/4$ allows for further simplified hardware. In particular, for digital finite-impulse-response (FIR) filter implementations, the impulse response of a half-band filter is zero for every other impulse response sample. The resulting hardware efficiencies allow for extremely high performance FIR filters having very linear, sharp-rolloff characteristics to be implemented for half-band filters 508 and 510 that are, at the same time, of a modest cost and complexity. In a preferred embodiment, a 67-tap FIR implementation is used having the remarkable rolloff characteristic that at 0.29 $F_s$ (only 0.04 $F_s$ above the cutoff frequency of 0.25 $F_s$), the attenuation is 90 dB.

It has been found that the use of a particular off-the shelf chip normally used in the telecommunications industry, and not formerly associated with usage in ultrasound systems, provides excellent results. The HSP 43216 chip is an off-the-shelf chip sold by Intersil Corp. of Melbourne, Fla., and has been found particularly adaptable for use an a demodulator according to the preferred embodiments. A single HSP 43216 chip can be used to implement the combination of the first stage local oscillator 502, the mixers 504 and 506, and the half-band filters 508 and 510. The datasheet for the HSP 43216 chip, Intersil File No. 3365.7 (January 1999), can be found on the Internet at www.intersil.com/data/fn/fn3/fn3365/fn3365.pdf, and application notes relevant to the HSP 43216 chip, Intersil File No. AN9063.2 (January 1999), can be found at www.intersil.com/data/an/an9/an9063/an9603.pdf. The contents of these documents are hereby incorporated by reference into the present disclosure.

Figure 2:
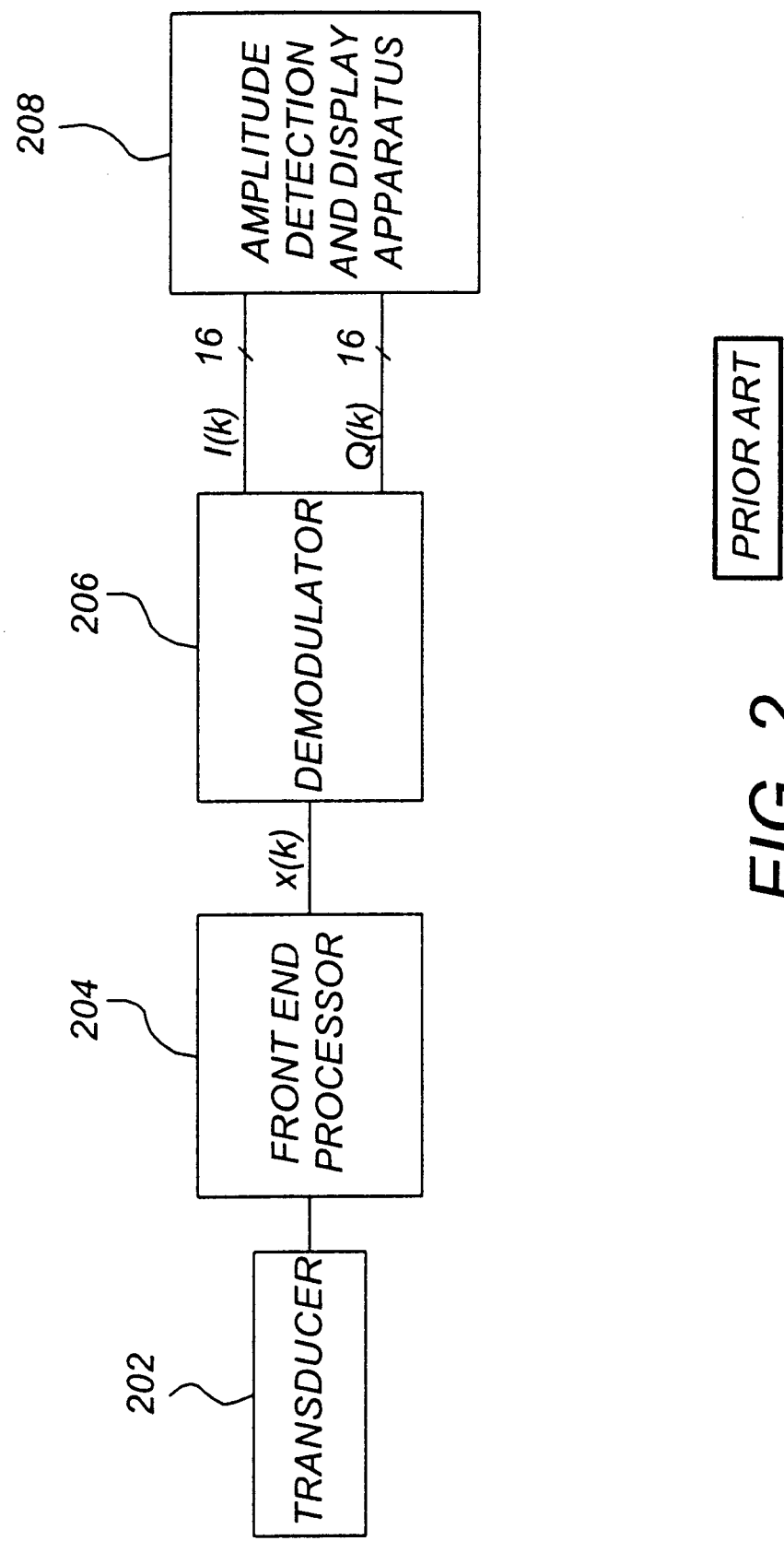
FIG. 2 is a block diagram of an ultrasound information processing system in accordance with prior art.

As shown in FIG. 5, the outputs of half band filters 508 and 510 are denoted as $I_f(k)$ and $Q_f(k)$, respectively, as they represent intermediate signals in the generation of the demodulator 500 output. Demodulator 500 further comprises a complex mixer 512 and a second stage local oscillator 514. Upon the creation of the signals $I_f(k)$ and $Q_f(k)$ at the outputs of half-band filters 508 and 510, these signals are then fed into the complex mixer 512 for rotation to the desired baseband signals I(k) and Q(k). The rotation is performed by mixing the signals $I_f(k)$ and $Q_f(k)$ with quadrature phase sinusoids, shown as cosine and sine in FIG. 5, that are generated by secondary local oscillator 514 at an advantageously selected mixing frequency of $F_s/4-F_x$. Here, $F_x$ may be a constant or varying frequency function, and is generally the same mixing frequency that would be used in the single-stage demodulator of FIG. 2. In other words, for Doppler processing $F_x$ is fixed at $F_x=F_c$, and for B-mode processing $F_x$ is set to a swept frequency function, in particular an instantaneous center frequency of the wideband input signal x(t) for better signal-to-noise performance.

Complex mixer 512 rotates the intermediate signals $I_f(k)$ and $Q_f(k)$ to the desired baseband signals I(k) and Q(k) by performing operations that accomplish the complex multiplication shown in Equation (11):

$$I(k)+jQ(k)=[I_i(k)+jQ_i(k)][\cos\{(\omega_s/4-\omega_x)kT\}-j\sin\{(\omega_s/4-\omega_x)kT\}] \quad \{11\}$$

In particular, in performing operations that accomplish the complex multiplication above, complex mixer 512 generates the in-phase component I(k) by performing the multiplies and adds shown in Equation (12), and generates the quadrature component by performing the multiplies and adds shown in Equation (13):

$$I(k)=I_i(k)\cos\{(\omega_s/4-\omega_x)kT\}+Q_i(k)\sin\{(\omega_s/4-\omega_x)kT\} \quad \{12\}$$

$$Q(k)=Q_i(k)\cos\{(\omega_s/4-\omega_x)kT\}-I_i(k)\sin\{(\omega_s/4-\omega_x)kT\} \quad \{13\}$$

Digital hardware for implementing complex mixer 512 generally comprises multiplier-accumulator circuitry for performing the above multiplies and adds which, in accordance with a preferred embodiment, are performed on 16-bit values and generate 16-bit results. One suitable hardware chip is the LMA1010 multiplier/accumulator chip available from Logic Devices. It is found to be advantageous for secondary local oscillator 514 to be implemented as a lookup table comprising a static random access memory (SRAM) to generate the sine and cosine signals at a frequency of $(F_s/4-F_x)$. In a preferred embodiment, the SRAM is 16K in size and stores 16 bit output values.

In operation, the SRAM address counter within secondary local oscillator 514 is reset for each transmit synchronization burst and then incremented at a frequency of $F_s$ during that burst interval. For Doppler mode operation, the SRAM simply provides the required sinusoidal values corresponding to a frequency of $F_s/4-F_x$, where $F_x$ is fixed at $F_c$. For B-mode imaging operations, the SRAM provides swept sinusoidal data for the depth frequency compensation function, i.e., for creating the appropriate mixing frequency $F_s/4-F_x$ where $F_x$ sweeps between maximum and minimum values during each burst interval.

Advantageously, in addition to providing Doppler and B-mode functionalities, the same SRAM and complex mixer hardware may be used (in conjunction with downstream low pass filter hardware, to be described infra) to achieve harmonic imaging mode functionality. This is accomplished by changing an offset frequency of the secondary local oscillator such that the frequency $F_x$ is swept at values near $2F_c$ which, as will be described further infra, allows information near the second harmonic of the carrier frequency to be isolated and observed.

Figure 3:
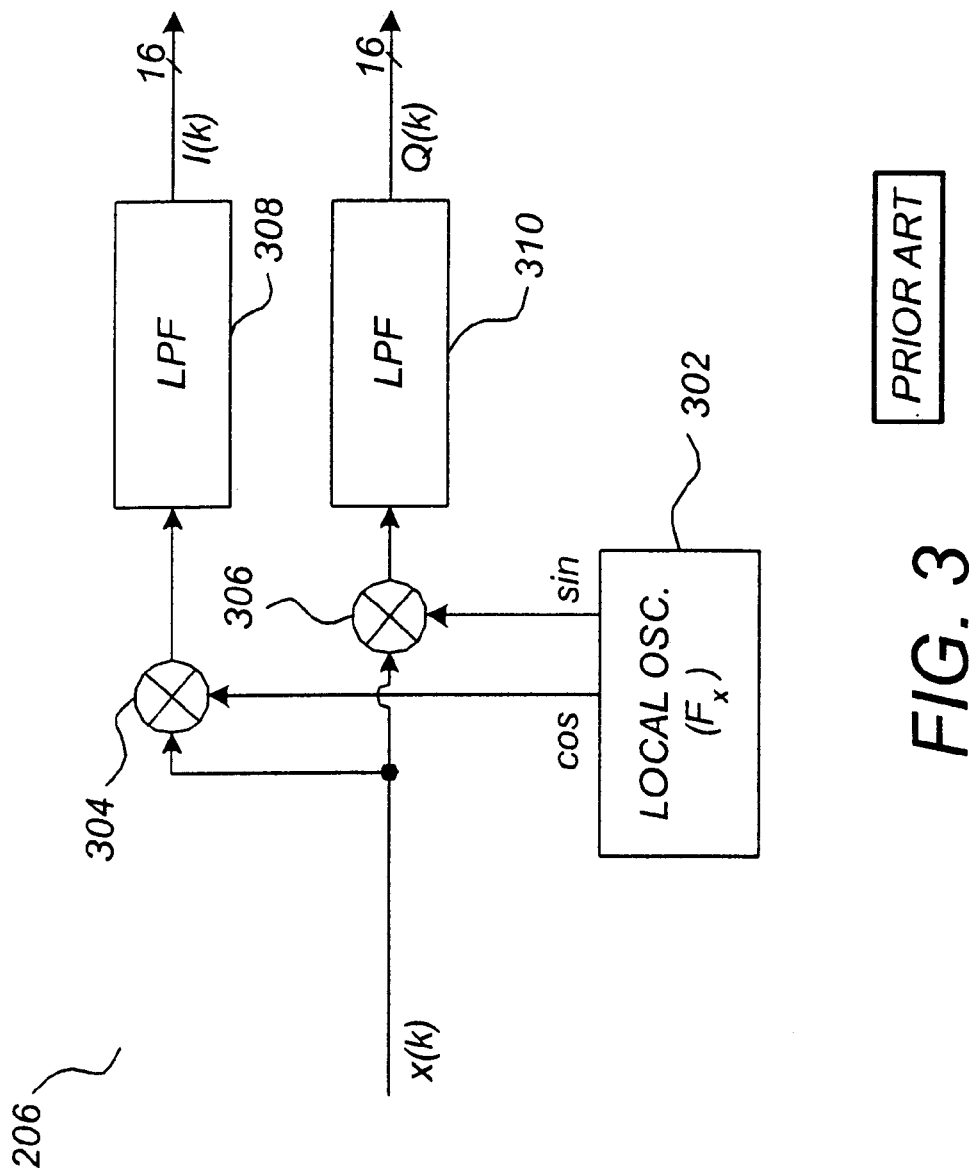
FIG. 3 is a block diagram of a demodulator used in the ultrasound information system of FIG. 2.
Figures 1, 6:
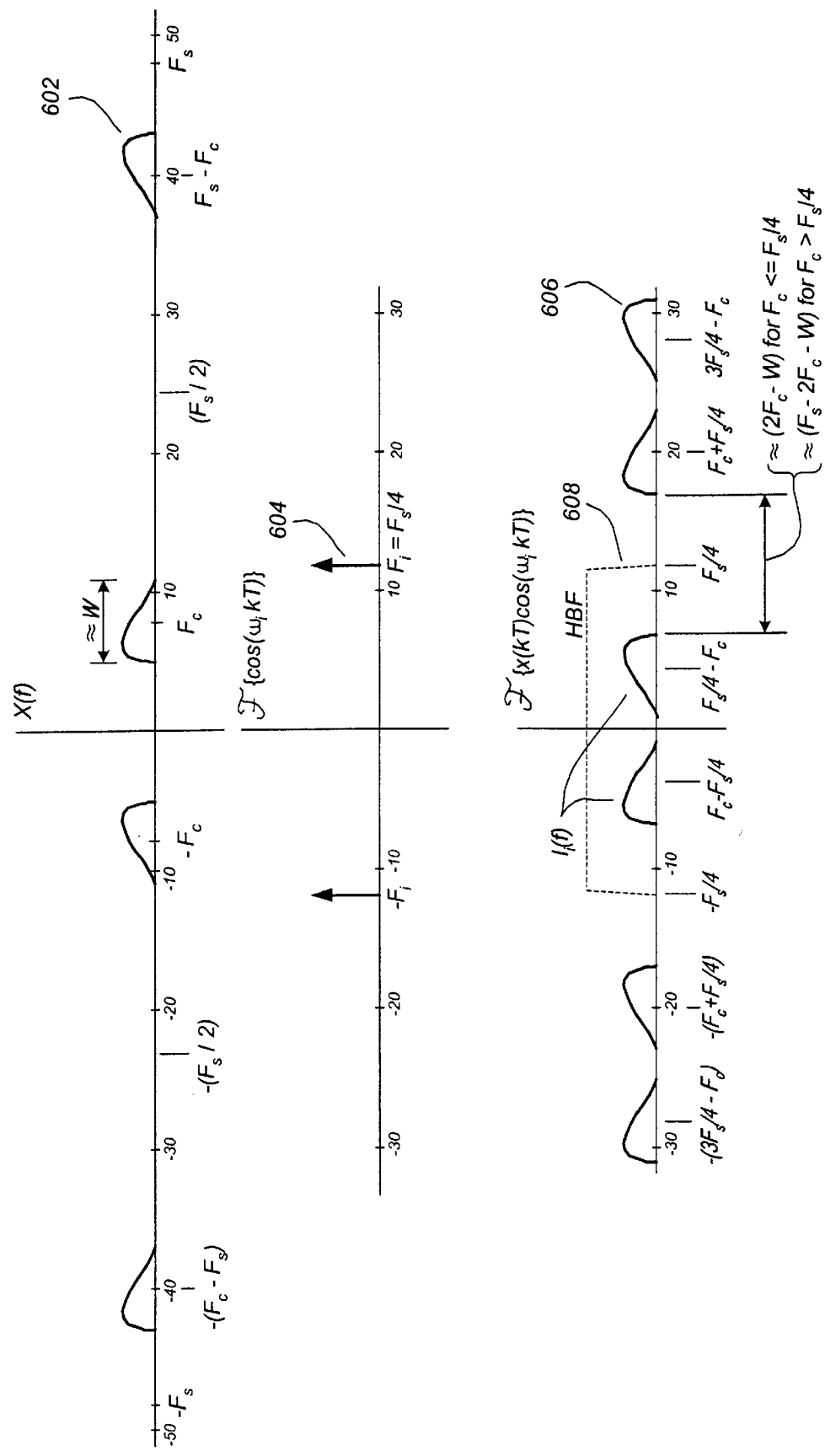
FIG. 6 comprises parts 6-1 through 6-4 and frequency spectra corresponding to the operation of the demodulator of FIG. 5.
Figures 2, 6:
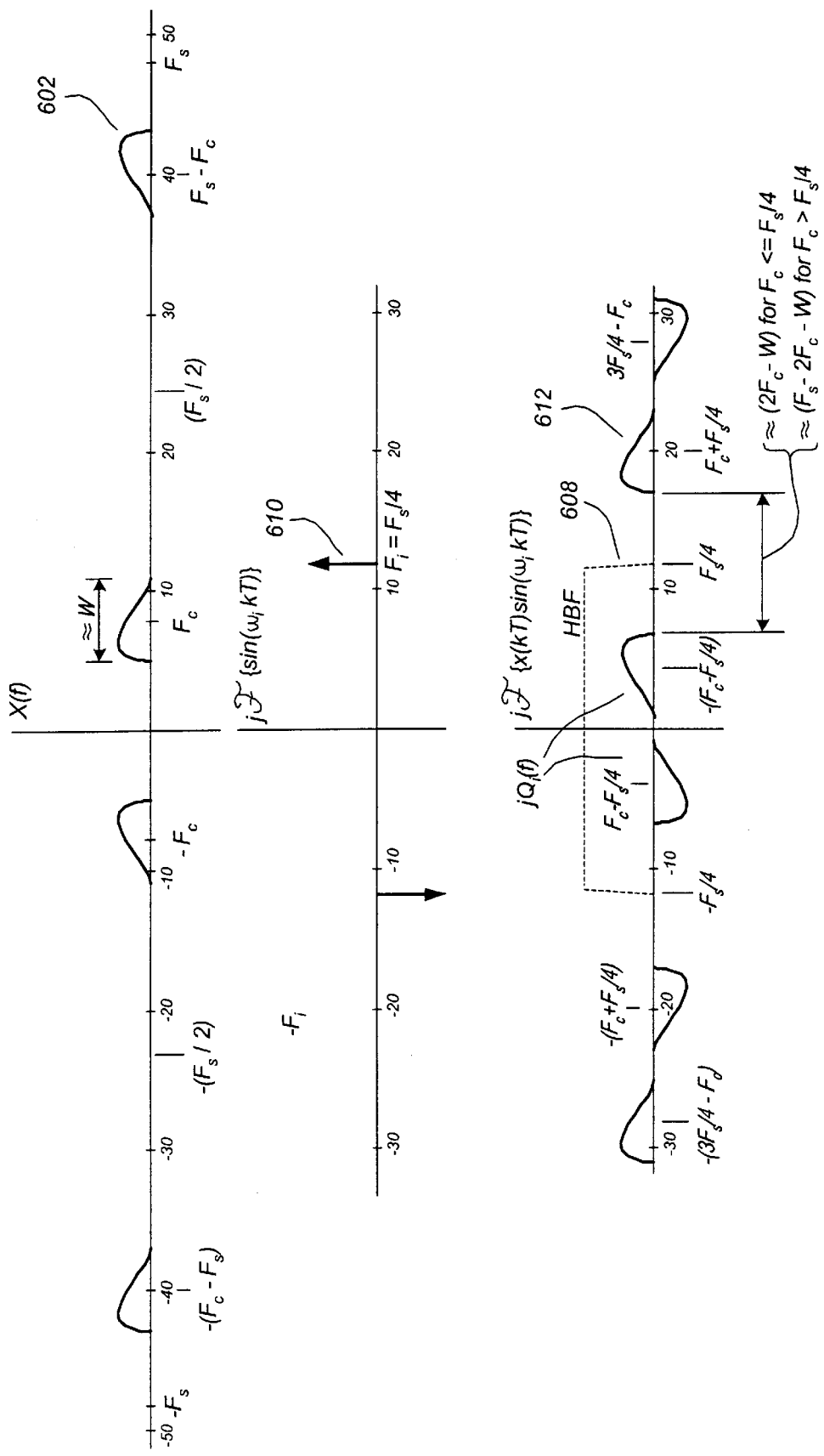
Figures 3, 6:
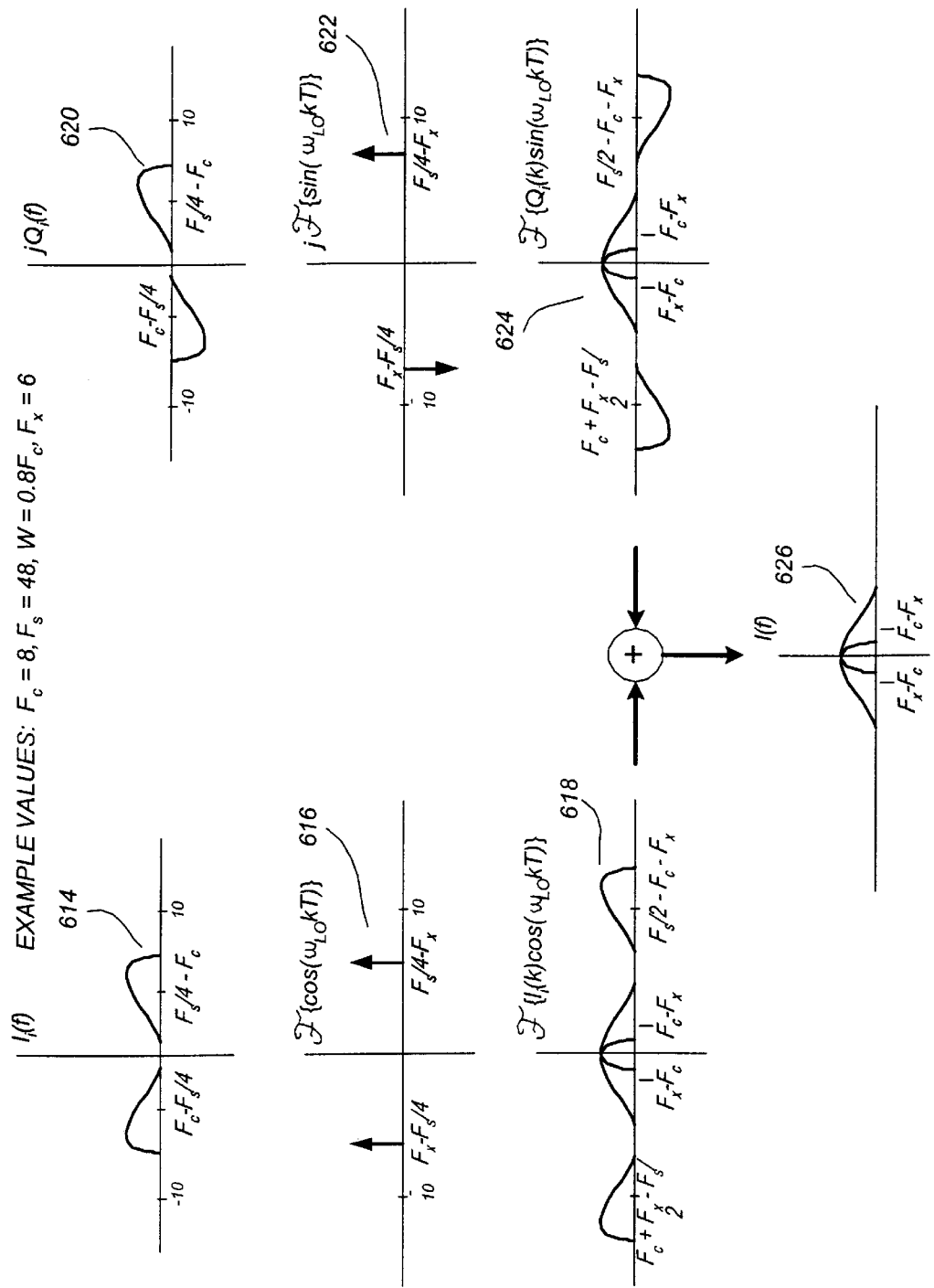
Figures 4, 6:
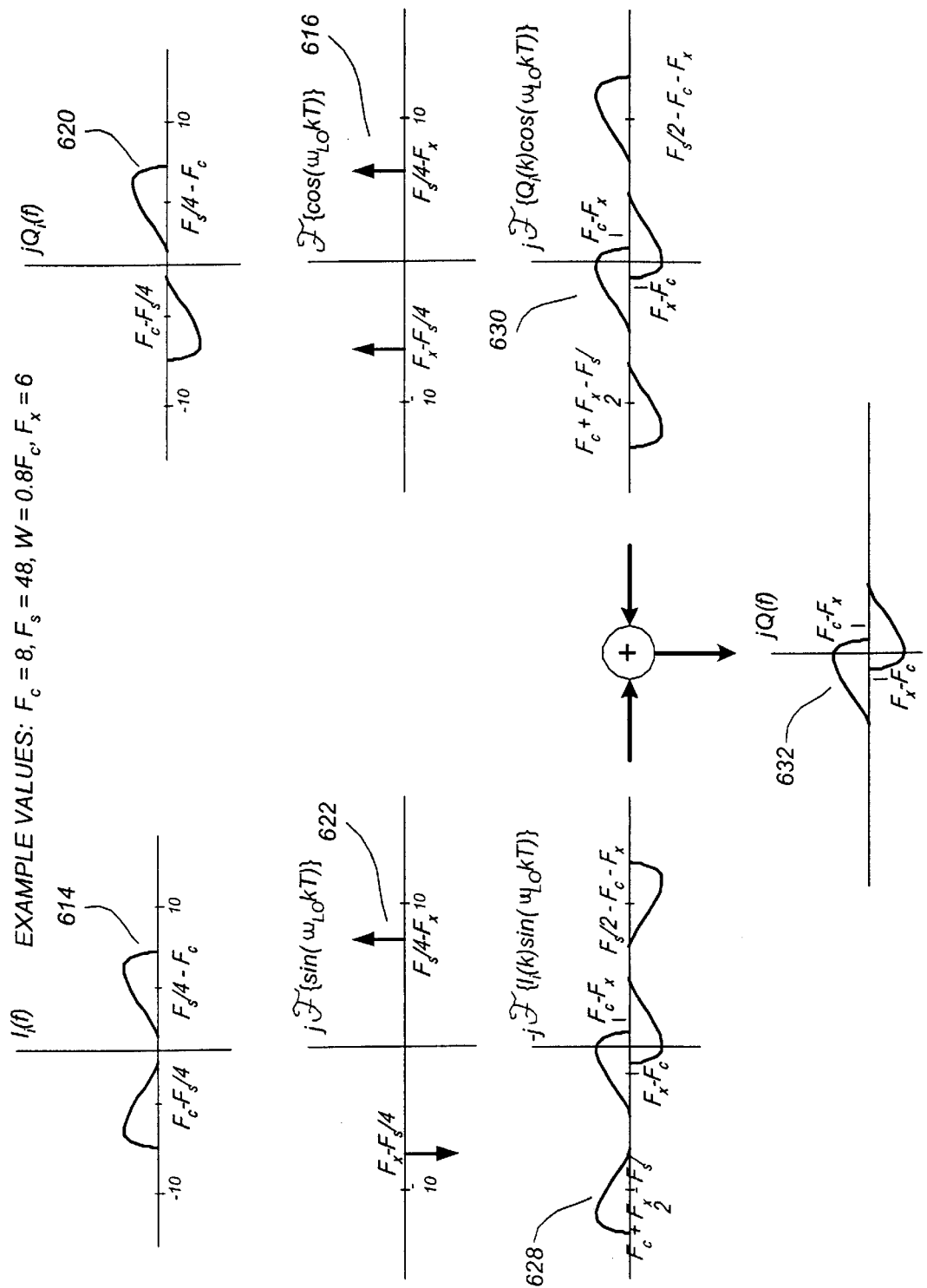

FIG. 6, comprising parts 6-1 through 6-4, shows spectrum plots corresponding to the operation of demodulator 500. FIG. 6 shows a first plot 602 of the Fourier transform of the RF signal x(k), a second plot 604 of the Fourier transform of the first stage local oscillator cosine term, and a third plot 606 of the Fourier transform of the mixer 504 output. FIG. 6 further shows a fourth plot 610 of the Fourier transform of the first stage local oscillator sine term, and a fifth plot 612 of the Fourier transform of the mixer 506 output. Upon being shifted in both directions by the intermediate frequency $F_i$, which is set to $F_s/4$ according to a preferred embodiment, the mixed signals 606 and 612 each contain a gap between the baseband portion and the undesired mirror portion approximately equal to $(2F_c-W)$ if $F_c<=F_s/4$, and approximately equal to $(F_s-2F_c-W)$ if $F_c>F_s/4$. In an example in which $F_c=8$ and $W=0.8F_c$, this gap is about 9.6 MHz. Importantly, however, despite the fact that this gap is similar to the gap at the mixer outputs of FIG. 3 in a similar example described supra, there is superior mirror cancellation according to the preferred embodiments. This is at least in part because each gap is symmetric around $F_s/4$, and therefore a half-band filter can be used having an extremely sharp rolloff at $F_s/4$. The passbands of the half-band filters 508 and 510, showing an exemplary steep rolloff, are shown as elements 608 superimposed on the plots 606 and 612 of FIG. 6.

Figures 1, 4:
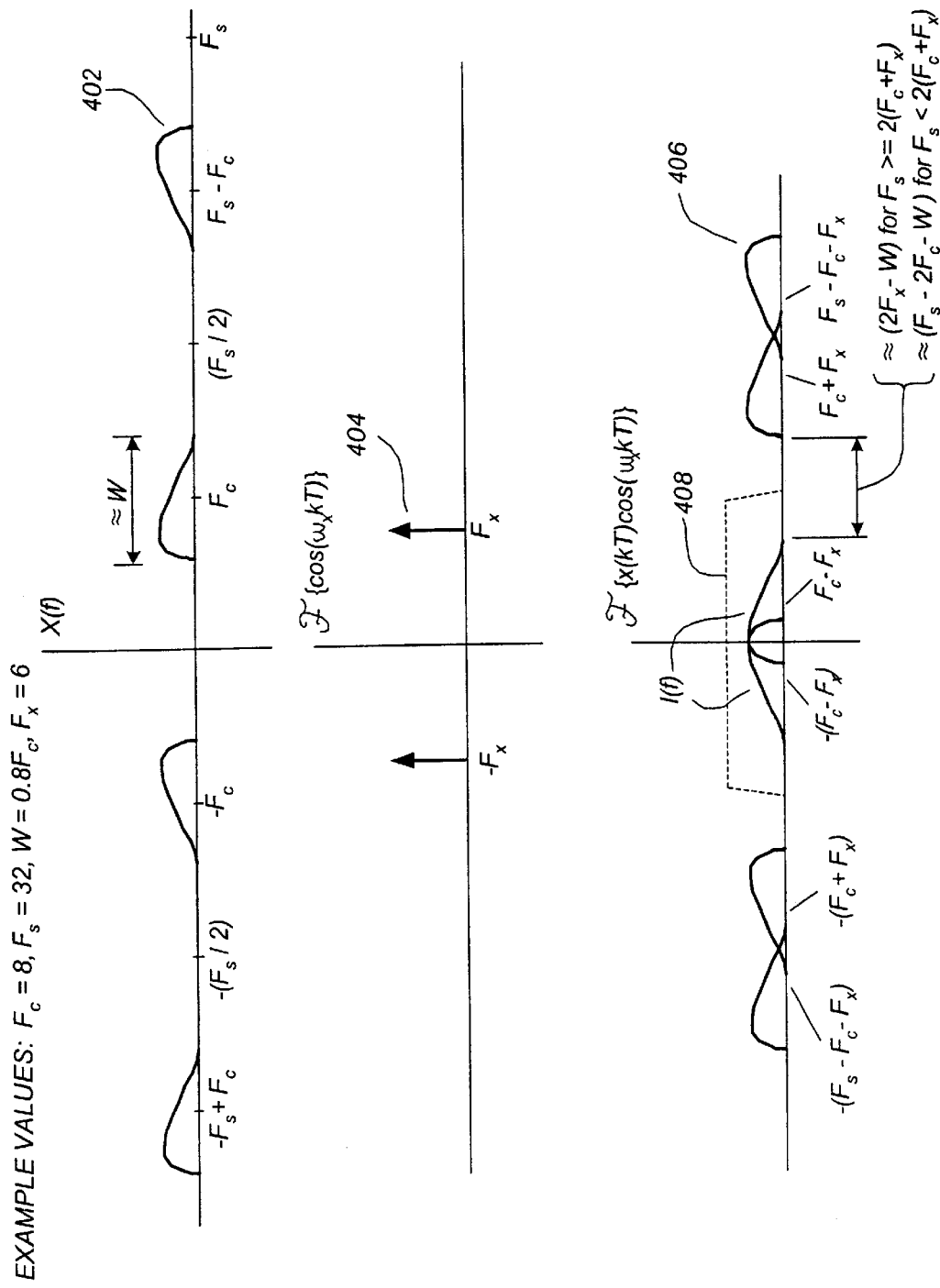
FIG. 4 comprises parts 4-1 and 4-2 and illustrates frequency spectra corresponding to the operation of the demodulator of FIG. 3.
Figures 2, 4:
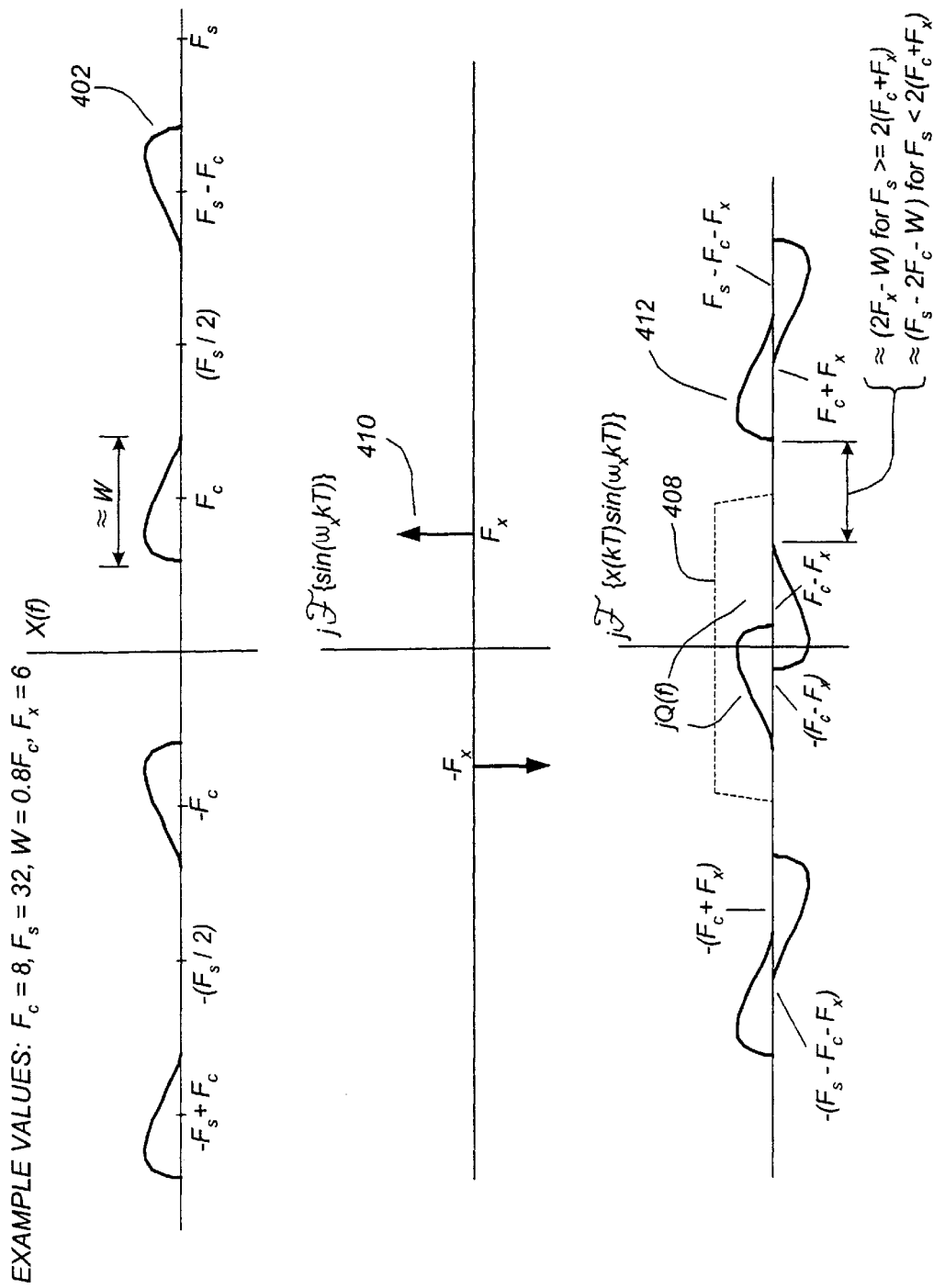

Also shown in FIG. 6 are frequency spectrum plots corresponding to the operation of complex mixer 512 of demodulator 500. FIG. 6 shows a frequency plot 614 of the output of half band filter 508, which corresponds to the intermediate in-phase signal $I_i(f)$, and a frequency plot 620 of the output of half band filter 510 multiplied by j, which corresponds to the intermediate quadrature phase signal $Q_i(f)$. Frequency plots 616 and 622 are also shown corresponding to the Fourier transforms of the outputs of secondary local oscillator 514. Additionally, frequency plots 618, 624, 628, and 630 are shown corresponding to the Fourier transforms of the intermediate multiplications performed in the complex mixer 512 indicated in Equations (12) and (13), supra. Finally, FIG. 6 shows a plot 626 of the Fourier transform of the in phase component output I(k) of complex mixer 512, and a plot 632 of the Fourier transform of the quadrature phase component output Q(k) of complex mixer 512. Advantageously, as can be seen by comparing plots 626 and 632 of FIG. 6 with plots 406 and 412 of FIG. 4, respectively, the frequency content of the signals at the baseband becomes identical to the desired baseband components for I(k) and Q(k) because of the selection of $(F_s/4-F_x)$ as the frequency for secondary local oscillator 514. Additionally, because the mirror canceling was performed by very sharp half band filters, the signals 626 and 632 of FIG. 6 represent "cleaner" outputs than the signals 406 and 412 of FIG. 4, and are also achieved using less expensive and less complex hardware in accordance with the preferred embodiments.

Figure 7:
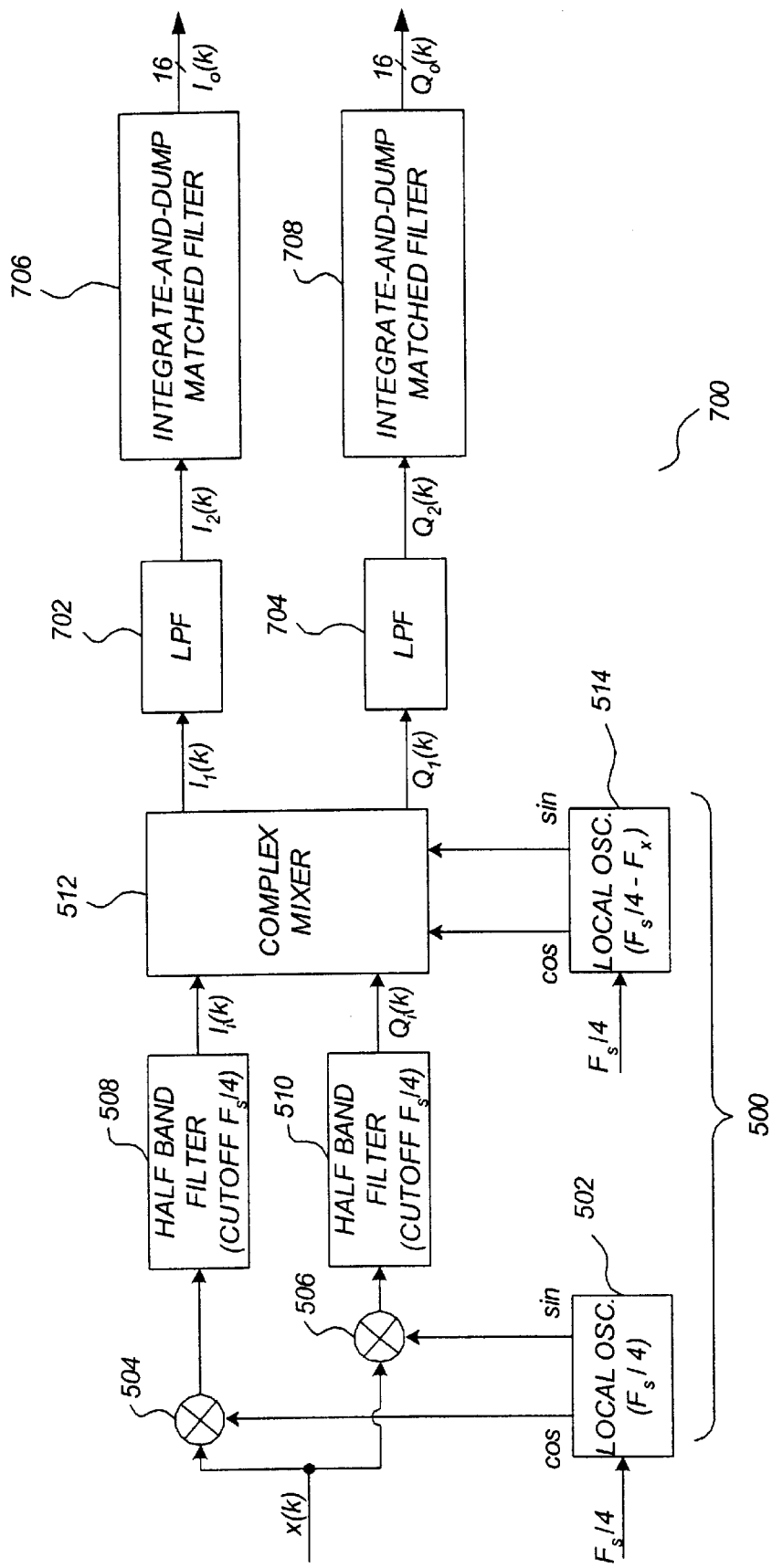
FIG. 7 is a block diagram of a demodulator in accordance with another preferred embodiment.

FIG. 7 shows a demodulator 700 for use in an ultrasound information processing system in accordance with another preferred embodiment. Demodulator 700 comprises substantially the demodulator 500 of FIG. 5, to which is coupled second stage low pass filters 702 and 704, along with integrate-and-dump matched filters 706 and 708, respectively. The additional components of demodulator 700 provide for further optimized output quality during Doppler and B mode processing as described herein, and additionally provide for harmonic imaging mode processing when used in conjunction with properly offset frequencies at the secondary local oscillator 514 as described infra. As shown in FIG. 7, the outputs of demodulator 500 are relabeled as $I_1(k)$ and $Q_1(k)$ to indicate that further processing is being performed to generate final demodulator outputs $I_o(k)$ and $Q_o(k)$ at the outputs of integrate-and-dump matched filters 706 and 708.

In a preferred embodiment, dual programmable low pass filters are used to implement the low pass filters 702 and 704. In hardware implementations, it is found useful to use the HSP 43168, a programmable 8-tap FIR filter available from Intersil Corp., supra. Such programmable filters allow for the shifting of the cutoff frequency as needs arise. During Doppler mode and B-mode imaging, the low pass filters 702 and 704 are set to appropriate bandwidths to provide further noise reduction and attenuation of spurious high frequencies. The low pass filters 702 and 704 will have cutoff frequencies that depend on the frequency of the signal received. For example, when an increase in depth is required, the receiving mean frequency is shifted down. Correspondingly, the bandwidth of the low pass filters 702 and 704 should be reduced.

Figure 8:
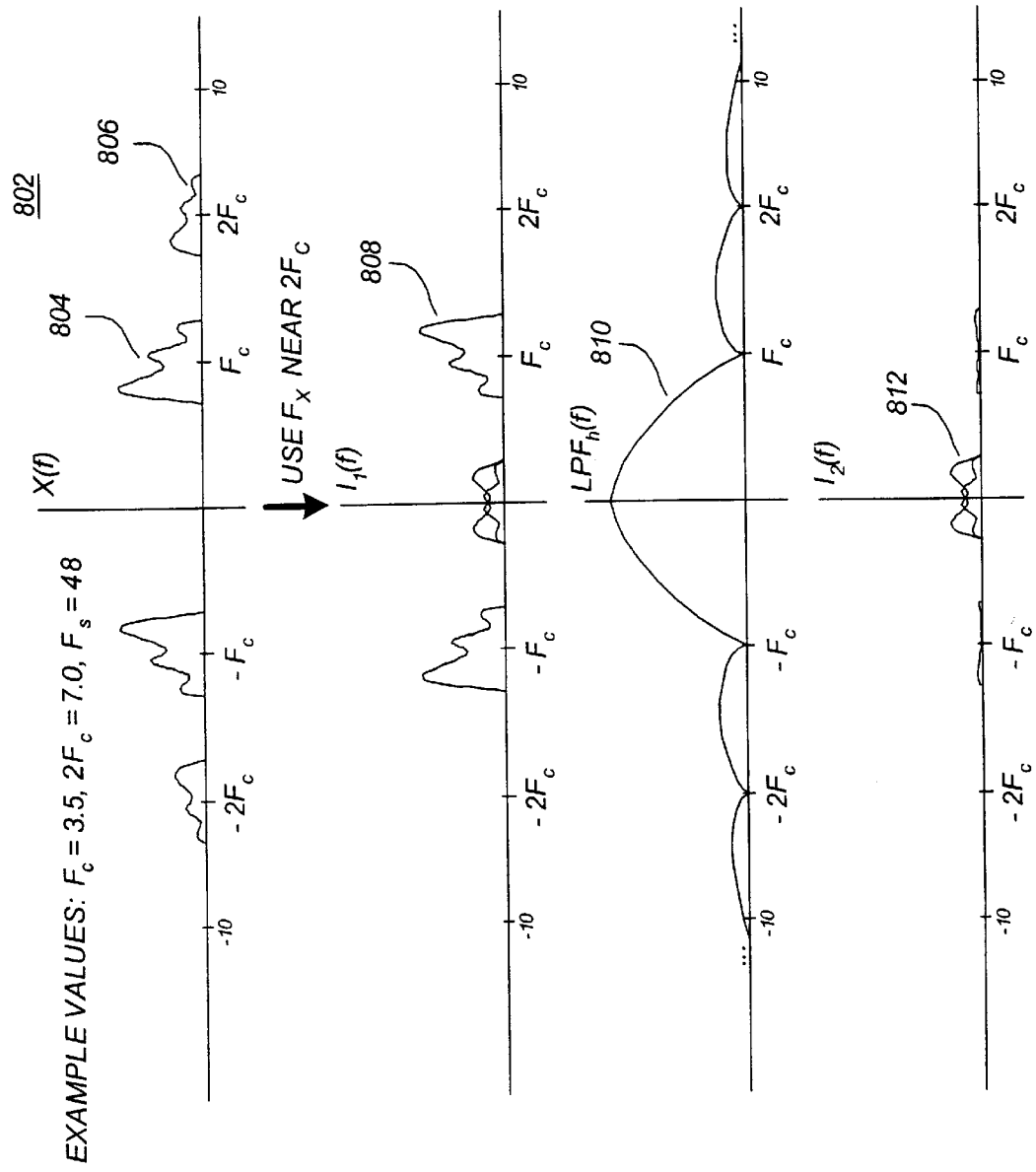
FIG. 8 illustrates frequency spectra corresponding to a harmonic imaging mode of the demodulator of FIG. 7 in accordance with a preferred embodiment.

FIG. 8 shows power spectra of the in phase signal component when propagating through the demodulator 700 in harmonic imaging mode in accordance with a preferred embodiment. Advantageously, the low pass filters 702 and 704, even though implemented using relatively inexpensive 8-tap FIR filters, can be readily adapted for use in conjunction with properly offset frequencies at the secondary local oscillator 514 to achieve harmonic imaging mode. Plot 802 of FIG. 8 shows the Fourier transform of a typical RF signal x(k) received during harmonic imaging mode, the RF signal x(k) having its first harmonic at a carrier frequency of 3.5 MHz (shown as plot element 804 in FIG. 8) and a second harmonic at 7 MHz (shown as plot element 806 and FIG. 8). In accordance with a preferred embodiment, the secondary local oscillator 514 generates frequencies of $(F_s/4-F_x)$, either swept or fixed in nature, such that $F_x$ is near the second harmonic $2F_c$. Using relationships established with respect to the description of demodulator 500 supra, it can be shown that the plot 808 results for in phase component $I_1(k)$ at the output of complex mixer 512. For simplicity and clarity of disclosure, only the in phase components are described with respect to harmonic imaging mode, it being understood that similar corresponding frequency contents will be experienced with the quadrature phase components. As shown in plot 808, it is the second harmonic components that are congregated near the origin of the frequency plot, while the first harmonic components are pushed out to $+F_c$ and $-F_c$.

In accordance with a preferred embodiment, for harmonic imaging mode the low pass filters 702 and 704 are programmed to have the spectrum 810 identified as $LPF_h(f)$ in FIG. 8 having a passband at the origin and first notches at $-F_c$ and $+F_c$. Advantageously, even though the low pass filters 702 and 704 are simple 8-tap FIR filters, the spectrum 810 is readily achieved having distinct zero pass notches at $-F_c$ and $F_c$. As shown in plot 812, which is a plot of the Fourier spectrum of signal $I_2(k)$ at the output of low pass filter 702, the first harmonic components of the RF signal x(k) are effectively removed and the second harmonic components are passed, thus achieving harmonic imaging mode functionality.

Figure 1A:
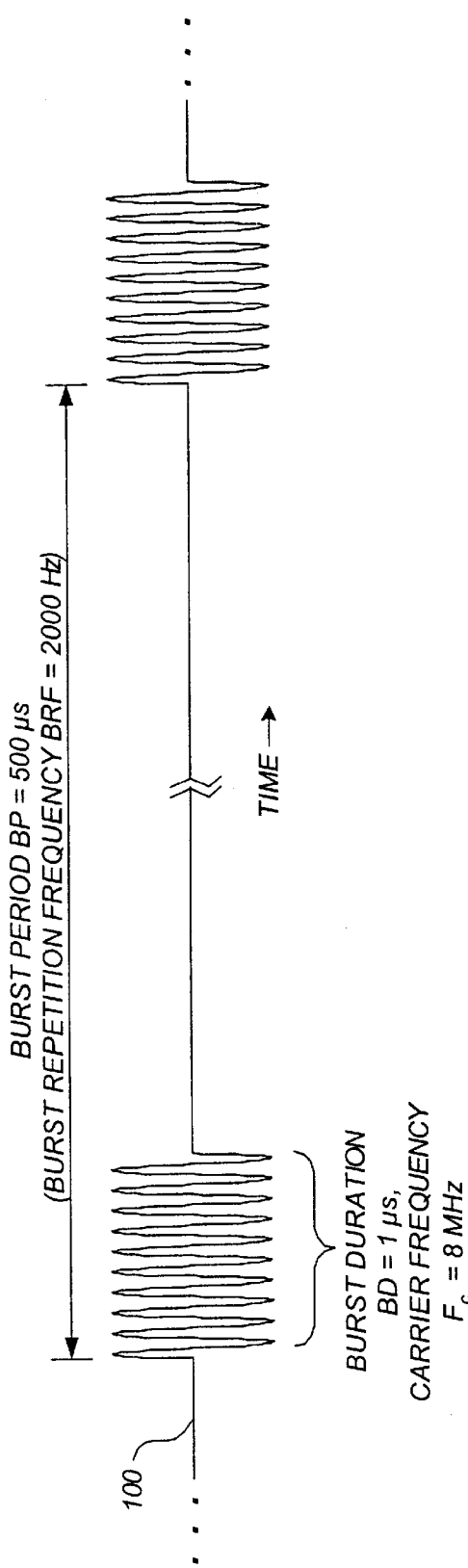
FIG. 1A illustrates an example of an ultrasound transducer input signal.
Figure 1B:
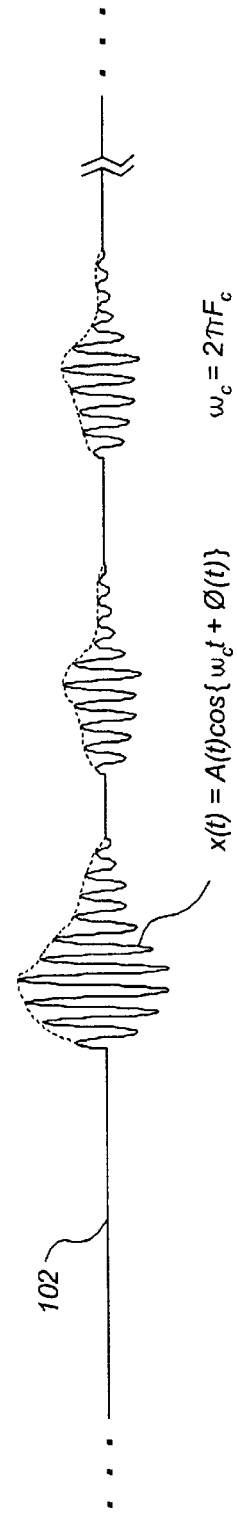
FIG. 1B illustrates an example of an ultrasound transducer output signal.
Figure 1C:
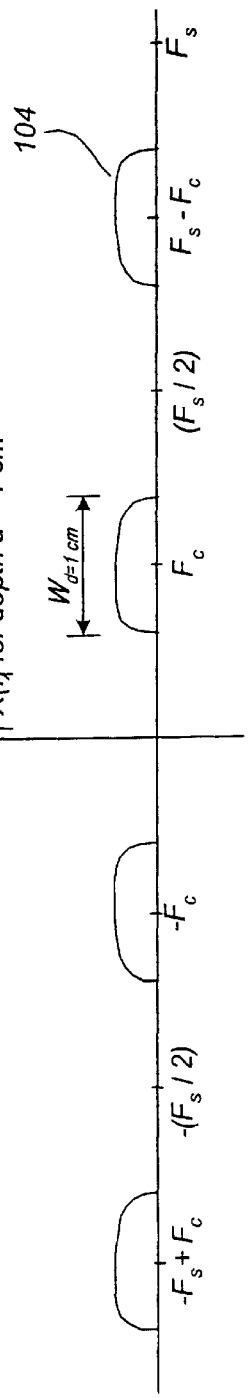
FIGS. 1C illustrates frequency spectra of portions of the output signal of an ultrasound transducer corresponding to differing target depths.
Figure 1C:
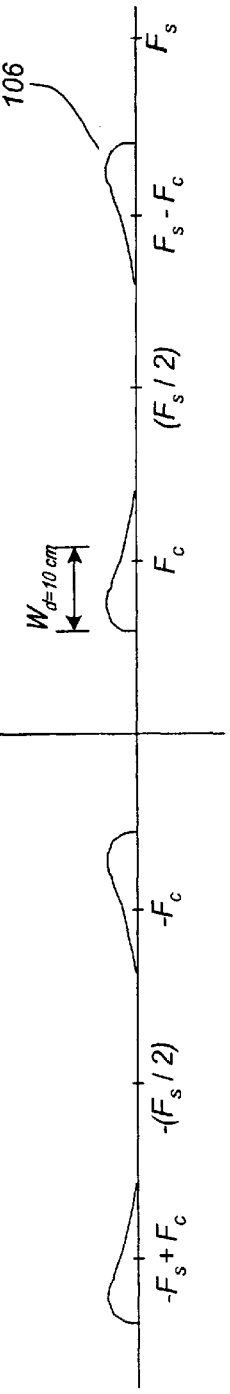
Figure 1C:
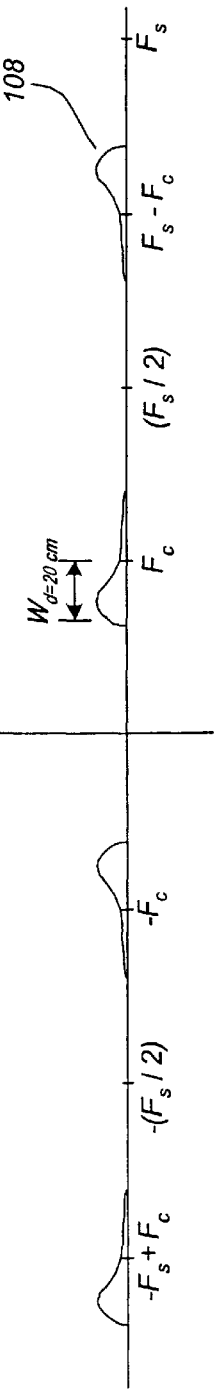

As shown in FIG. 7, the signals $I_2(k)$ and $Q_2(k)$ at the outputs of low pass filters 702 and 704, respectively, are fed into integrate-and-dump matched filters MF 706 and 708, respectively. Integrate-and-dump matched filters are known in the art, and a description can be found in Couch, *Digital And Analog Communications Systems*, 3rd ed. (MacMillan 1990) at pp. 497–503, the contents of which are hereby incorporated by reference into the present application. Generally speaking, the integrate-and-dump matched filters 706 and 708 provide for increased signal-to-noise ratio through matched filtering using an assumption that the transmitted pulse is a square wave for the burst duration BD (see FIG. 1A). Additionally, the integrate-and-dump matched filters 706 and 708 provide for an integration or averaging function of the data for subsequent image display, as demodulation operations at the sampling frequency $F_s$ in accordance with the preferred embodiments results in more data than needed for visual display on most current ultrasound display equipment. Integrate-and-dump matched filters 706 and 708 are adjusted dependent on the display pixel density desired. For example, the filtered output may be further filtered at a lower cut-off frequency to prevent spatial aliasing on the display screen. With such an implementation, contrast resolution on the display screen is also improved.

In accordance with another preferred embodiment, the demodulator signals I(k) and Q(k) at the output of demodulator 500 or 700 can be used by downstream circuitry in B-mode imaging to produce useful flow information, as follows. In particular, a phase detection circuit performs a $\tan^{-1}[Q(k)/I(k)]$ operation to determine phase information of the demodulated signal. Due to the large number of bits each signal has (16 bits each in a preferred embodiment), each signal is first compressed from a 16 bit number to an 8 bit number by going through a RAM look up table to implement the $\tan^{-1}[Q(k)/I(k)]$ function. An amplitude detection circuit likewise computes the amplitude using Equation (7). The instantaneous phase and amplitude for each sample for an entire ultrasound frame are stored in memory as the next frame is being processed. The phase information at each sample position is then correlated (or compared) with the same sample position in the last frame. If there is blood flow at that sample position, the phase will be different from frame to frame. The stationary tissue shows no (or very little) phase change. The amplitude information can be used to modify the phase correlation output to reject the noise, e.g. when the amplitude is small, the phase may be meaningless. The final output combines the gray scale amplitude information and color temporal phase information to display the B-mode with blood flow. This method is in contrast to the conventional color flow map, which relies on the Doppler effect of the flow, or other art that uses amplitude correlation for B-flow. The described phase application in B-mode, while not computing precise phase information at each sample position in each ultrasound frame, nevertheless produces useful flow information by taking advantage of the temporal distinctions between two successive frames. This is in contrast to other art which processes the phase information along the axis of the beam, as one is in the spatial domain and the other is in a frame-based temporal domain.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments are not intended to limit their scope, which is limited only by the scope of the claims set forth below.

What is claimed is:

1. A demodulator for use in an ultrasound information processing system, said demodulator for receiving an input signal comprising digital samples, the digital samples being taken at a sampling frequency from an ultrasound transducer output, said demodulator for generating a demodulated output signal from said input signal, said demodulator comprising:

a quadrature mixing device, said quadrature mixing device having a mixing frequency of one quarter of said sampling frequency, said quadrature mixing device comprising a half-band filter having a cutoff frequency of one-quarter of said sampling frequency, said quadrature mixing device for performing mirror-cancellation on said digital samples to produce intermediate signals; and a complex mixer for rotating said intermediate signals to a baseband frequency to produce an in-phase component and a quadrature phase component of said demodulated output signal;

whereby an amplitude of said demodulated output signal corresponds to the vector magnitude of said in-phase component and said quadrature component.

2. The demodulator of claim 1, said ultrasound transducer generating acoustic bursts at a carrier frequency, wherein said complex mixer has a mixing frequency equal to one quarter of the sampling frequency minus a first frequency function, whereby said demodulated output signal contains frequency components substantially near a frequency equal to said carrier frequency minus said first frequency function.

3. The demodulator of claim 2, said half-band filter of said quadrature mixing device being a first half-band filter, said quadrature mixing device comprising:
- a first mixer for multiplying said digital samples with a first sinusoid, said first mixer having an output coupled to an input of said first half-band filter;
- a second mixer for multiplying said digital samples with a second sinusoid in quadrature phase with said first sinusoid; and
- a second half-band filter, said second half-band filter having an input coupled to an output of said second mixer;

wherein said intermediate signals comprise an in-phase intermediate signal at the output of said first half-band filter and a quadrature-phase intermediate signal at the output of said second half-band filter.

4. The demodulator of claim 3, wherein said first mixer, said second mixer, said first half-band filter, and said second half-band filter are implemented on a single hardware chip, and wherein said first and second half-band filters are implemented in said hardware chip by finite impulse response filters having at least 40 taps.

5. The demodulator of claim 4, wherein said sampling frequency is greater than 40 MHz.

6. The demodulator of claim 2 wherein, an a Doppler processing mode, said first frequency function is fixed at said carrier frequency.

7. The demodulator of claim 6 wherein, in a B-mode processing mode, said first frequency function is a swept frequency function between a minimum frequency value and a maximum frequency value.

8. A demodulator for use in an ultrasound information processing system, said ultrasound system comprising an ultrasound transducer generating acoustic bursts at a carrier frequency, the ultrasound transducer receiving acoustic echo signals and generating an input signal therefrom, the ultrasound information processing system digitizing the input signal at a sampling frequency to generate digital samples, said demodulator comprising:
- a quadrature mixer adapted to multiply said digital samples with quadrature-phase sinusoids at one quarter of said sampling frequency and filter the results with half-band filters each having a cutoff frequency of one-quarter of said sampling frequency to produce mirror-canceled signals; and
- a complex mixer for rotating said mirror-canceled signals to baseband to produce complex mixer output signals, whereby amplitude and phase information of a demodulated signal can be derived from said complex mixer output signals.

9. The demodulator of claim 8, further comprising:
- a secondary local oscillator for producing mixing signals that are mixed with the mirror-canceled signals by the complex mixer, said mixing signals being sinusoids at a frequency equal to the carrier frequency minus a first frequency function; and
- for each complex mixer output signal, a programmable low-pass filter;

wherein, in a harmonic imaging mode, said first frequency function is set substantially near a frequency equal to twice the carrier frequency;

and wherein, in said harmonic image mode, said programmable low-pass filter is adapted to have a notch at the carrier frequency for producing a programmable low-pass filter output having suppressed first harmonic information and passed second harmonic information from said input signal.

10. The demodulator of claim 9, further comprising, for each programmable low-pass filter, an integrate-and-dump matched filter coupled to the output thereof for enhancing signal to noise performance of said demodulator.

11. The demodulator of claim 10, said demodulator also having a Doppler processing mode, wherein in said Doppler processing mode said first frequency function of said secondary local oscillator is fixed at said carrier frequency.

12. The demodulator of claim 11, said demodulator also having a B-mode processing mode, wherein in said B-mode processing mode said first frequency function is a swept frequency function between a minimum frequency value and a maximum frequency value.

13. The demodulator of claim 12, wherein said quadrature mixer is implemented on a first hardware chip having an at-least 40 tap finite impulse response (FIR) half-band filter, and wherein said programmable low-pass filter is implemented on a second hardware chip having substantially fewer taps than said first hardware chip, whereby said demodulator has reduced implementation cost by using fixed half-band filters for mirror canceling while using programmable digital filters in locations that do require a high number of FIR filter taps.

14. The demodulator of claim 13, wherein said sampling frequency is greater than 40 MHz.

15. A method for demodulating an ultrasound signal, said ultrasound signal having a carrier frequency, comprising the steps of:
- sampling said ultrasound signal at a sampling frequency to produce digital samples;
- mixing said digital samples with quadrature-phase signals at frequency equal to one-quarter of the sampling frequency;
- filtering results of said mixing step with half-band filters each having a cutoff frequency at one-quarter of the sampling frequency to produce mirror-canceled signals; and
- rotating said mirror-canceled signals to baseband using a complex mixer.

16. The method of claim 15, wherein said sampling frequency is at least four times greater than said carrier frequency.

17. The method of claim 16, further comprising the step of, prior to the step of sampling, filtering said ultrasound signal with an anti-aliasing filter having a cutoff frequency not greater than half the sampling frequency.

18. The method of claim 17, said step of rotating comprising the step of mixing said mirror-canceled signals with quadrature-phase sinusoids having a frequency equal to one-fourth of said carrier frequency minus a first frequency function, said first frequency function being equal to said carrier frequency in a Doppler mode, and said first frequency function being a swept frequency function a B-mode.

19. The method of claim 18, said first frequency function being substantially near twice the carrier frequency in a harmonic imaging mode.

20. The method of claim 19, further comprising the step of, in said harmonic imaging mode, low-pass-filtering at least one of said rotated signals with a low-pass filter having a notch at the carrier frequency for producing an output having suppressed first harmonic information and passed second harmonic information from said input signal.

21. An imaging method comprising:

sending ultrasound energy into a body, receiving from the body ultrasound energy related to interactions between the body and the ultrasound energy sent therein, and deriving an input signal related to the received ultrasound energy;

converting the input signal into digital samples related to a sampling frequency;

processing the digital samples through a digital quadrature mixer using first mixing signals at a frequency of approximating a quarter of the sampling frequency to produce quadrature mixer outputs;

filtering the quadrature mixer outputs through at least one digital filter having a passband approximately half the sampling frequency to produce intermediate digital signals;

processing the intermediate digital signals through a complex mixer to produce complex mixer outputs;

processing the complex mixer outputs to derive estimates of information related to at least one of an envelope of the input signal and a phase of the input signal; and using the estimates to generate and display an image related thereto.

22. A method as in claim 21 in which the filtering comprises filtering the mixer outputs through at least one digital half-band filter.

23. A method as in claim 22 in which the processing of the complex mixer outputs comprises processing the complex mixer output through at least one low pass filter to produce low pass filter outputs.

24. A method as in claim 22 including processing the low pass filter outputs through at least one integrate-and-dump matched filter.

25. A method as in claim 21 in which the processing of the intermediate signals through the complex mixer comprises mixing the intermediate signals with second mixing signals at a frequency approximating the algebraic sum of quarter the sampling frequency and a frequency function.

26. A method as in claim 25 in which the imaging comprises a Doppler mode, and the frequency function is fixed.

27. A method as in claim 25 in which the imaging comprises a B-mode and the frequency function varies in a manner related to changes in an instantaneous frequency of the input signal.

28. An ultrasound imaging system comprising:

a transducer sending ultrasound energy into a body and receiving from the body ultrasound energy related to interactions between the body and the ultrasound energy sent therein, said transducer producing an input signal related to the ultrasound energy received thereby;

a converter receiving the input signal produced by the transducer and deriving therefrom digital samples related to a sampling frequency;

a source of first mixing signals at a frequency approximating a quarter of the sampling frequency;

a digital quadrature mixer receiving the first mixing signals and the digital samples and in response producing quadrature mixer outputs related thereto;

at least one digital filter receiving and filtering the quadrature mixer outputs to provide a passband approximately half the sampling frequency and thereby produce intermediate digital signals;

a source of second mixing signals;

a digital complex mixer receiving the second mixing signals and the quadrature mixing outputs to produce complex mixer outputs;

a detector receiving and processing the complex mixer outputs to derive estimates of information related to at least one of an envelope of the input signal and a phase of the input signal; and a display displaying information related to the estimates of at least one of the envelope and the phase.

29. A system as in claim 28 in which the digital filter comprises at least one digital half-band filter.

30. A system as in claim 28 in which the complex mixer comprises at least one low pass filter produce low pass filter outputs.

31. A system as in claim 30 including at least one integrate-and-dump matched filter processing the low pass filter outputs.

32. A system as in claim 28 in which the source of the second mixing signals comprises a source of signals at a frequency approximating the algebraic sum of quarter the sampling frequency and a frequency function.

33. A system as in claim 32 in which the source of the second mixing signals produces signals at fixed frequency for system operation in a Doppler mode but at a frequency varying in a manner related to changes in an instantaneous frequency of the input signal for system operation in a B-mode.

* * * * *